United States Patent
Chang et al.

(10) Patent No.: US 9,579,022 B2
(45) Date of Patent: *Feb. 28, 2017

(54) WEARABLE ELECTRONIC DEVICE

(71) Applicant: Rooti Labs Limited, Cayman (KY)

(72) Inventors: Ming-Shiung Chang, New Taipei (TW); Ko-Mai Li, New Taipei (TW); Shu-Chen Chuang, New Taipei (TW)

(73) Assignee: Rooti Labs Limited, Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,863

(22) Filed: May 19, 2015

(65) Prior Publication Data

US 2016/0073882 A1 Mar. 17, 2016

(30) Foreign Application Priority Data

Sep. 12, 2014 (CN) .......................... 2014 1 0463431

(51) Int. Cl.
*A61B 5/00* (2006.01)
*G06F 1/16* (2006.01)

(52) U.S. Cl.
CPC .......... *A61B 5/0015* (2013.01); *A61B 5/6802* (2013.01); *A61B 5/6814* (2013.01); *A61B 5/6822* (2013.01); *A61B 5/6824* (2013.01); *G06F 1/163* (2013.01); *A61B 5/681* (2013.01); *A61B 5/683* (2013.01); *A61B 5/6804* (2013.01); *A61B 2560/0443* (2013.01)

(58) Field of Classification Search
CPC ..... A61B 5/0015; A61B 5/6838; A61B 5/002; A61B 5/02438; A61B 5/0245
See application file for complete search history.

(56) References Cited

U.S. PATENT DOCUMENTS

| 2015/0094558 A1* | 4/2015 | Russell | A61B 5/688 600/391 |
| 2015/0105221 A1* | 4/2015 | Roush | G06Q 50/22 482/8 |

* cited by examiner

*Primary Examiner* — Leon Flores
(74) *Attorney, Agent, or Firm* — Zhigang Ma (57) ABSTRACT

A wearable electronic device includes a signal capturing assembly and a wearable assembly. The signal capturing assembly is configured for detecting and processing vital signs from a user and defines at least one port. The signal capturing assembly includes a base, a first cover, a second cover, a third cover, a first electrode, and a core module. The first, second, third covers cover the base to form a receiving chamber to accommodate the core module. The first electrode is extended through the base and electronically connected to the core module The wearable assembly is detachably connected to the signal capturing assembly through the at least one port.

15 Claims, 8 Drawing Sheets

WEARABLE ELECTRONIC DEVICE

CROSS-REFERENCE TO RELATED APPLICATION

This application is related to co-pending U.S. patent application Ser. No. 14/714,861, entitled "WEARABLE ELECTRONIC DEVICE", and invented by Chang et al. The related application has the same assignee as the present application and has been concurrently filed herewith. The above-identified application is incorporated herein by reference in its entirety.

FIELD

The subject matter herein generally relates to wearable electronic devices, and particularly to a wearable electronic device that can be worn various ways.

BACKGROUND

Electronic devices are commonplace throughout most of the world today. Advancements in integrated circuit technology have enabled the development of electronic devices that are miniaturized and are small enough to be attached or coupled to the wrist, neck and head of users or integrated into clothes of the users.

BRIEF DESCRIPTION OF THE DRAWINGS

Many aspects of the present disclosure can be better understood with reference to the drawings. The components in the drawings are not necessarily drawn to scale, the emphasis instead being placed upon clearly illustrating the principles of the disclosure. Moreover, in the drawings, like reference numerals designate corresponding parts throughout the views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 1:
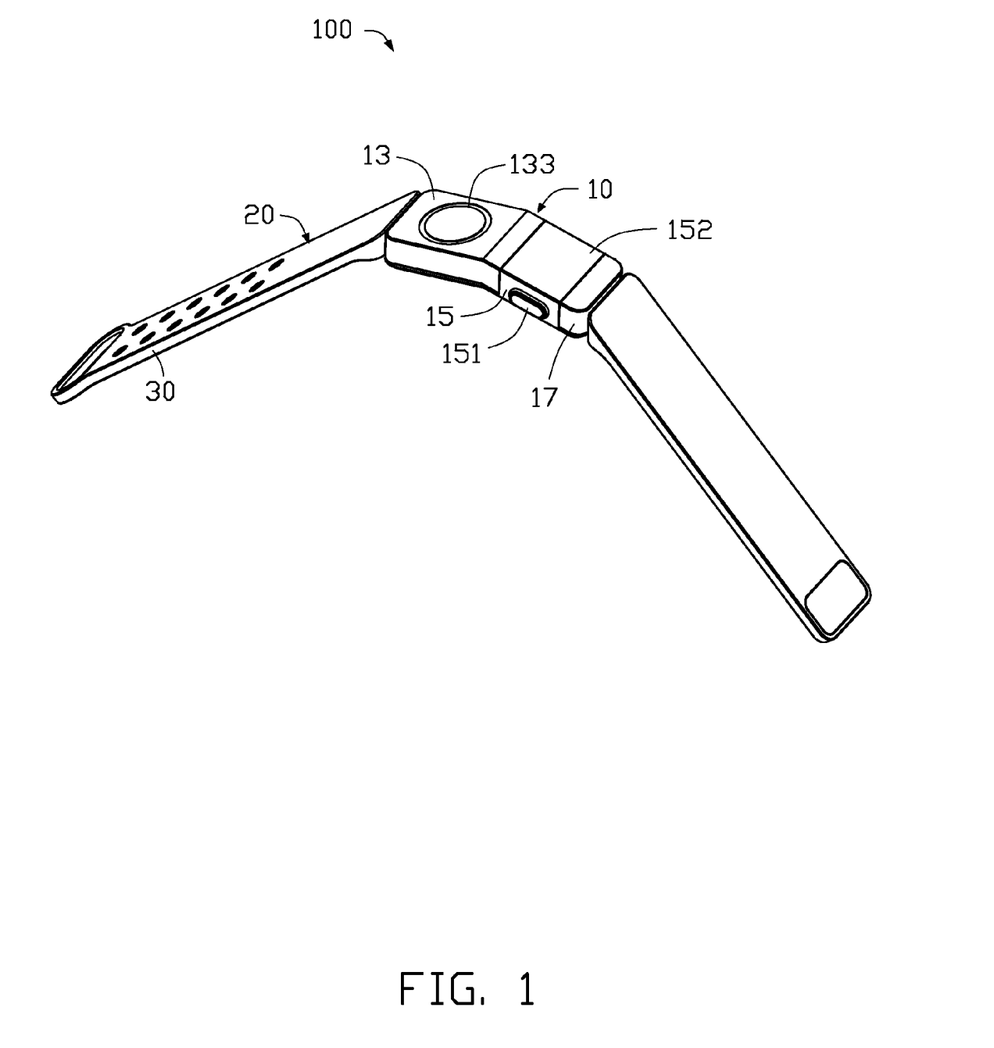
FIG. 1 is an isometric view of a wearable electronic device, according to a first exemplary embodiment.

FIG. 1 is an isometric view of a wearable electronic device 100, according to a first exemplary embodiment. The electronic device 100 can be a smart watch, a health monitor, or a smart pendant. The wearable electronic device 100 includes a signal capturing assembly 10, a wearing assembly 20, and an accessory 70 (shown in FIG. 3). The signal capturing assembly 10 is configured for detecting and processing vital signs of a user (such as heart rate, temperature, pulse, blood pressure and so on), but may include/provide other functionality as is known in the mobile/wearable electronics arts. The wearable assembly 20 is detachably connected to the signal capturing assembly 10 and configured to be worn by a user. The accessory 70 is detachably connected to the signal capturing assembly 10 and configured for charging the signal capturing assembly 10 and transmitting the processed vital signs from the signal capturing assembly 10 to other electronic device such as a mobile phone, or a computer.

Figure 2:
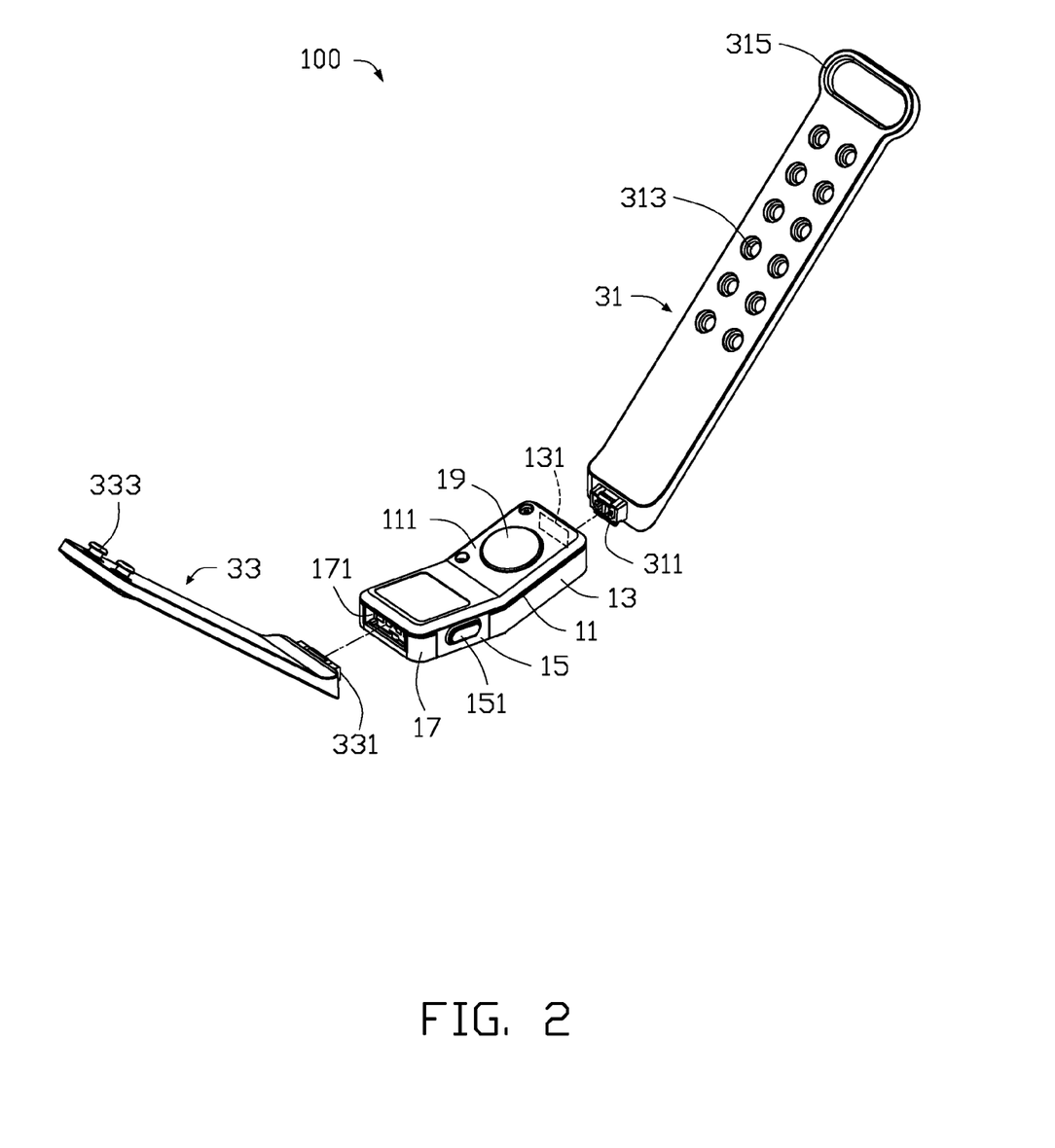
FIG. 2 is an exploded view of the wearable electronic device of FIG. 1.
Figure 8:
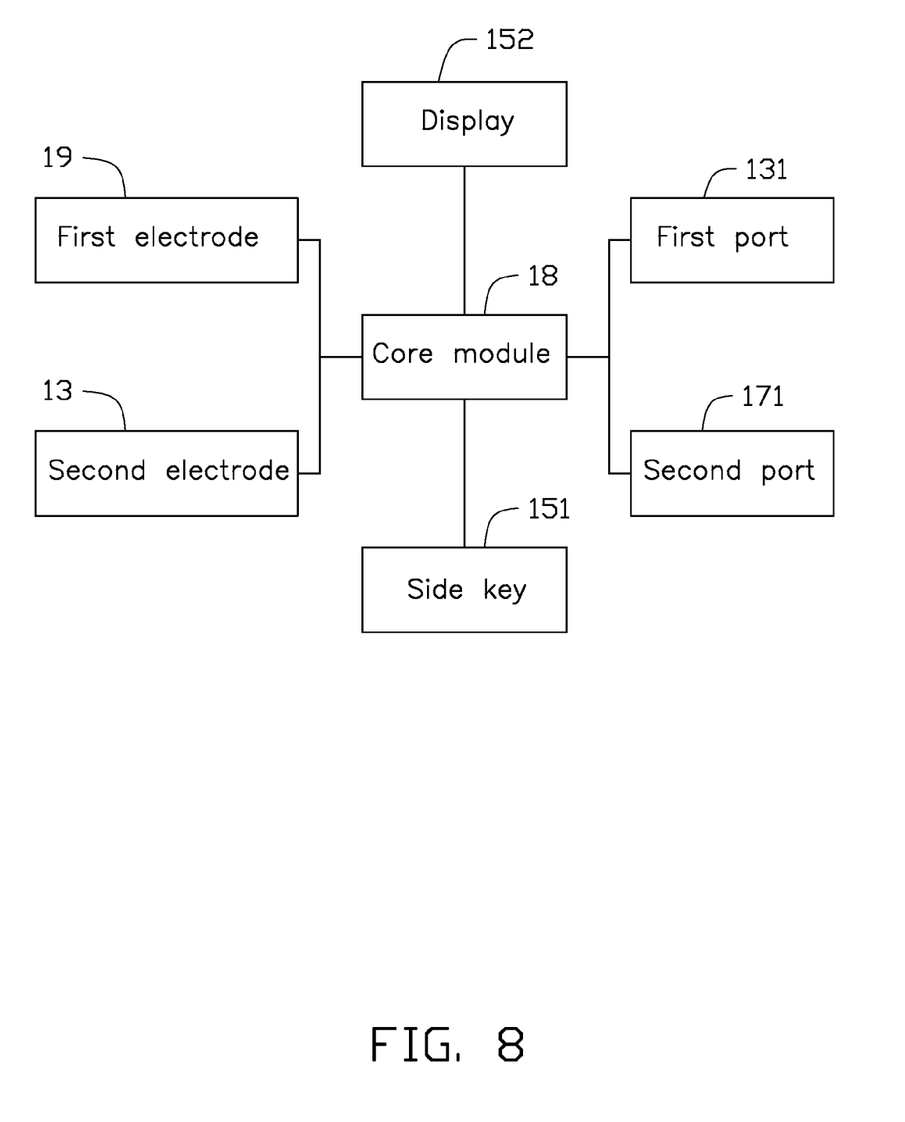
FIG. 8 is block diagram of the wearable electronic device of FIG. 1.

FIG. 2 illustrates that the signal capturing assembly 10 includes a base 11, a first cover 13, a second cover 15, a third cover 17, a first electrode 19. Signal assembly also includes a core module 18 (shown in FIG. 8).

The base 11 is a substantially bent plate having a first bending portion in a middle portion of the base 11 (best see FIG. 2). In this exemplary embodiment, an obtuse angle is formed at the first curved portion so that the signal capturing assembly 10 can be fit on a wrist of a user. A sealing layer 111 is arranged on an outer surface of the base 11. The sealing layer 111 is made of rubber. The first, second, third covers 13, 15, 17 cover the base 11 to define a receiving chamber to accommodate the core module 18, wherein the first and third covers 13, 17 are made of conductive material, and the second housing 15 is made of plastic material. The first cover 13 has a second curved portion corresponding to the first bending portion. The first cover 13 serves as a second electrode of the signal capturing assembly 10 and is electronically connected to the core module 18.

A ring-shaped button 133 (shown in FIG. 5) is positioned on a surface of the first cover 13 and configured for labeling a contact position of the first cover 13. The first electrode 19 extends through a bottom surface of the base 11 and is electrically connected to the core module 18. When the button 133 is pressed by fingers of the user, a loop through the body of the user is formed between the first electrode 19 and the second electrode so that the first electrode 19 detects the vital signs of the user and transmits the detected vital signs to the core module 18. The core module 18 detects the vital signs and processes functions of the signal capturing assembly 10. In addition, the core module 18 can also instigate a vibrating function of the signal capturing assembly 10. In other embodiment, a finger of the left hand and a finger of the right hand of the user are respectively attached to the first electrode 19 and the second electrode to formed the loop between the first electrode 19 and the second electrode.

A first port 131 is positioned at an end of the first cover 13. The first port 131 has a latching slot configured for detachably connecting to the wearable assembly 20. A side key 151 is arranged at one side of the second cover 15. The side key 151 is electronically connected to the core module 18 and configured for powering on/off the signal capturing assembly 10 or setting working parameters of the core module 18. A display 152 is arranged on a surface of the second cover 15. The display 152 is electronically connected to the core module 18 and configured for displaying a health state of the user based on the vital signs, the working parameters of the core module 18, and so on. A second port 171 similar to the first port 131 is positioned at an end of the third cover 17 configured for detachably connecting to the wearable assembly 20 or the accessory 70.

In this exemplary embodiment, the wearable assembly 20 is a wrist assembly 30 that allows the signal capturing assembly 10 to be attached to the wrists of the user. The wrist assembly 30 includes a first band 31 and a second band 33. A first connector 311 is positioned at an end of the first band 31. The first connector 311 is latched to the first port 131 thereby connecting the first band 31 to the signal capturing assembly 10. A latching ring 315 is positioned on another end of the first band 31 opposite to the first connector 311. A plurality of positioning holes 313 are defined in the first band 31. A second connector 331 is positioned at an end of the second band 331. The second connector 331 is latched to the second port 171 thereby connecting the second band 33 to the signal capturing assembly 10. A plurality of positioning members 333 are arranged at another end of the second band 331. The positioning members 333 are configured for engaging with the positioning holes 313 so that the signal capturing assembly 10 can be sleeved on and attached to the wrist of the user. However, the subject matter is not limited to straps 31 and 33. Other designs as is known in the art that include only a single strap or band, multiple straps or the like for securing a wearable device to a wrist or ankle could be used. The invention is not limited to any particular type of attachment structure.

Figure 3:
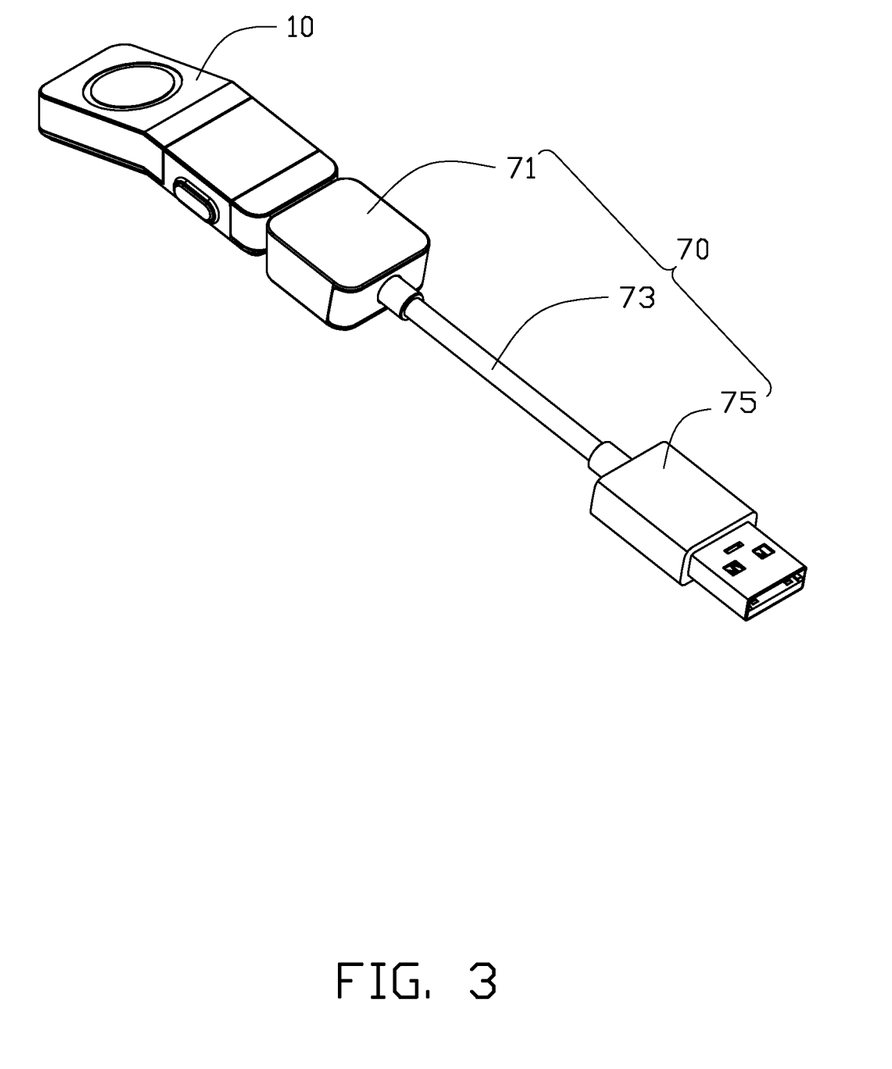
FIG. 3 is an isometric view of an accessory of the wearable electronic device of FIG. 1.
Figure 4:
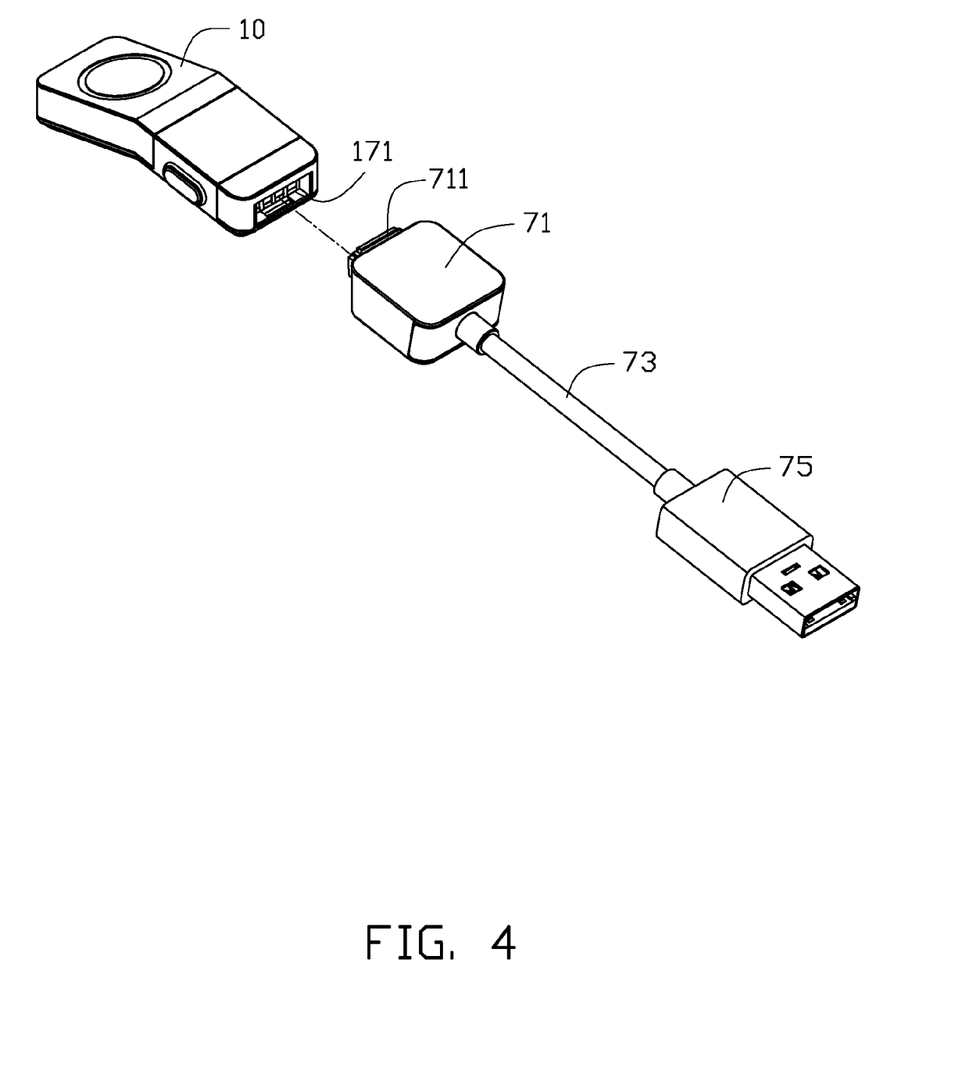
FIG. 4 is an exploded view of the accessory of FIG. 3.

FIGS. 3 and 4 illustrate that the accessory 70 includes a first connecting portion 71, a cable 73, and a second connecting portion 75 (which may be a USB adapter or other known connector). The first and second connecting portions 71, 75 are connected to two opposite ends of the cable 73. A rib 711 protrudes from an end of the first connecting portion 71 opposite to the second connecting portion 75. The rib 711 is configured for latching the first connecting portion 71 to the second port 171. The first connecting portion 71 can be electronically connected to the core module 18 by the second port 171 so that the signal capturing assembly 10 can be charged or connected to other electronic devices by the accessory 70. The second band 33 and the accessory 70 can both be connected to the second port 171. To charge the signal capturing assembly 10 or connect the signal capturing assembly 10 to the other electronic devices, the second band 33 is detached from the signal capturing assembly 10 and the accessory 70 is assembled to the signal capturing assembly 10.

Figure 5:
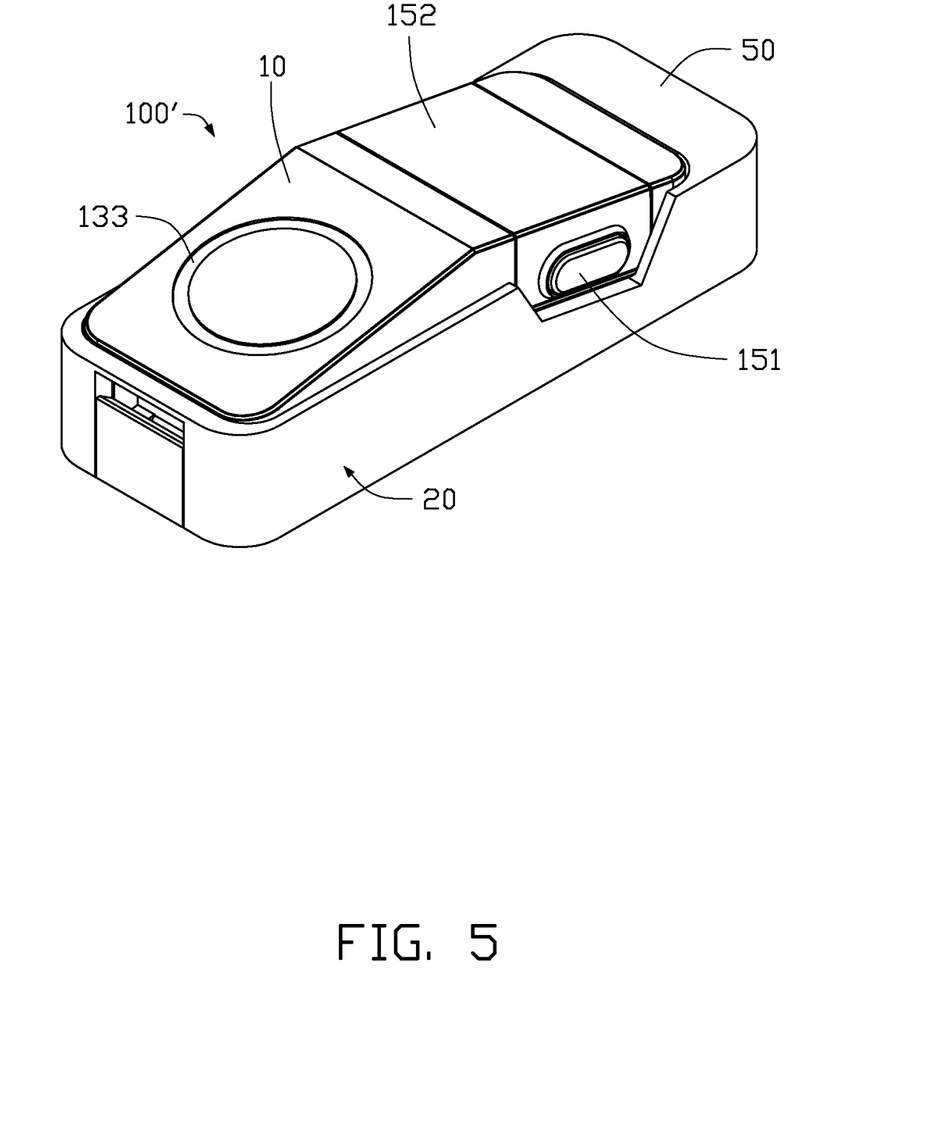
FIG. 5 is an isometric view of a wearable electronic device, according to a second exemplary embodiment.

FIG. 5 is an isometric view of a wearable electronic device 100', according to a second exemplary embodiment. The structure of the wearable electronic device 100' is substantially similar to that of the wearable electronic device 100 and includes a signal capturing assembly 10, a wearing assembly 40, and an accessory 70. The difference is that the wearing assembly 40 of the wearable electronic device 100' is a holder 50. The holder 50 is configured for attaching the wearable electronic device 100' to clothes of the users or an electronic patch so that the wearable electronic device 100' can be worn under the clothes.

Figure 6:
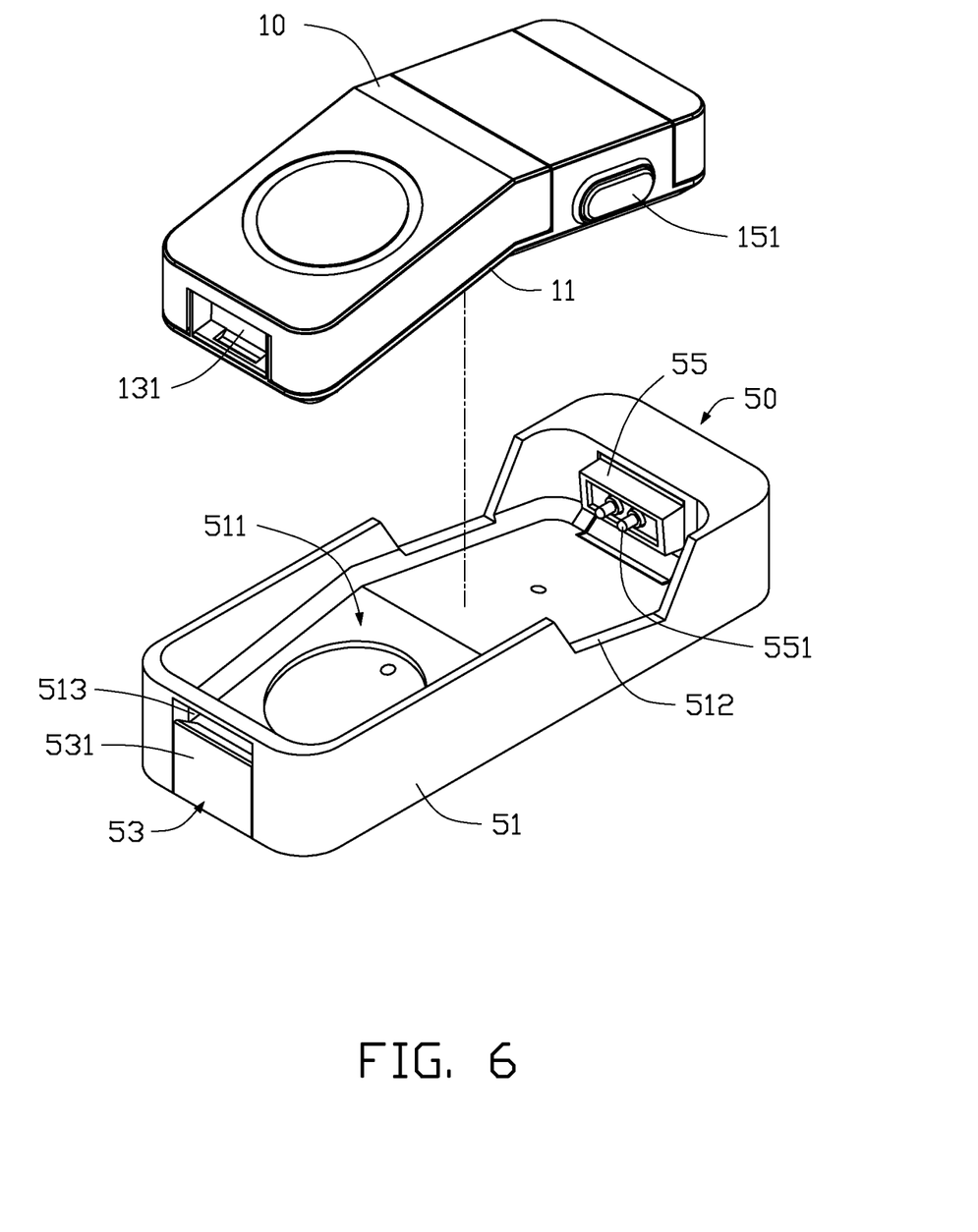
FIG. 6 is an exploded view of the wearable electronic device of FIG. 5.
Figure 7:
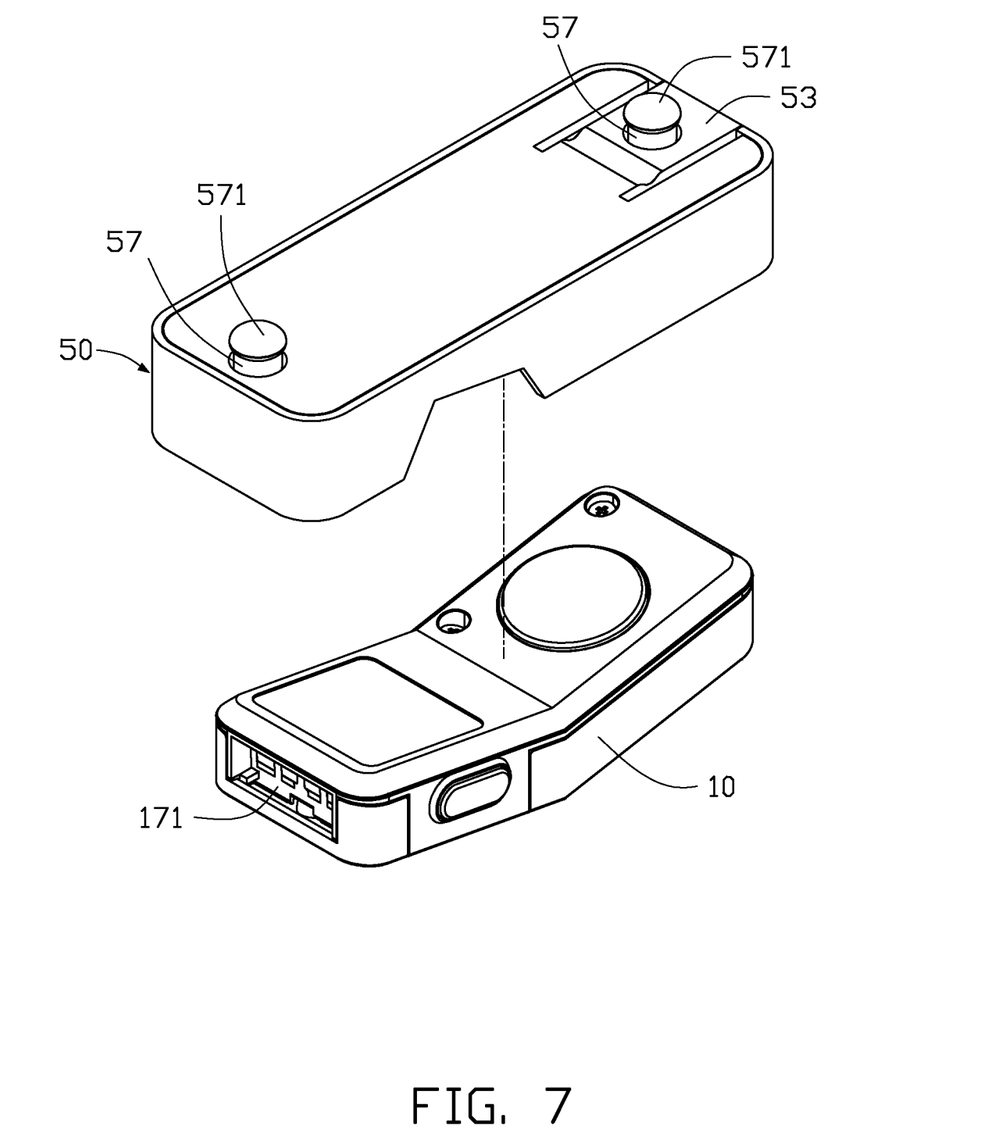
FIG. 7 is similar to FIG. 5, but shown from another angle.

FIGS. 6 and 7 illustrate that the holder 50 includes a case 51. A receiving slot 511 is defined in the case 51 and configured for receiving the signal capturing assembly 10. Two opposite cutouts 512 are defined in two opposite sidewalls of the case 512. The side key 151 is exposed from one of the cutouts 512. The cutouts 512 are configured for conveniently operating the side key 151 and remove the signal capturing assembly 10 from the receiving slot 511. A through hole 513 is defined in an end of the case 512. A latching member 53 is secured on a bottom surface of the case 51 with a latching portion 531 exposed from the through hole 513 for latching to the first port 131. A convertor 55 is arranged at another end of the case 51 opposite to the through hole 513 and configured to connect to the second port 171 of the signal capturing assembly 10. The convertor 55 includes two contacting rods 551 protruding from the case 51 configured for electrically connecting to core module 18. Two connecting electrodes 57 are arranged on the bottom surface of the case 51. One of the connecting electrodes 57 is extended through the latching member 53. Each connecting electrode 57 includes a protrusion 571 protruding from the bottom surface of the case 51. The connecting electrodes 57 are electronically connected to the contacting rods 551 and configured for integrating the signal capturing assembly 10 to the clothes of the users so that the signal capturing assembly 10 can be worn under the clothes.

In this exemplary embodiment, the convertor 55 and the accessory 70 share the second port 171. To charge the signal capturing assembly 10 or connect the signal capturing assembly 10 to the other electronic device, the signal capturing assembly 10 is removed from the holder 50, and accessory 70 is connected to the second port 171.

The wearable electronic device 100 can be worn various ways by connecting the signal capturing assembly 10 to either the wrist assembly 30 or the holder 50.

It is to be understood, however, that even through numerous characteristics and advantages of the present disclosure have been set forth in the foregoing description, together with details of assembly and function, the disclosure is illustrative only, and changes may be made in the details, especially in the matters of shape, size, and arrangement of parts within the principles of the disclosure to the full extent indicated by the broad general meaning of the terms in which the appended claims are expressed.

What is claimed is:
1. A wearable electronic device comprising:
a signal capturing assembly defining at least one port and configured for detecting and processing vital signs from a user, the signal capturing assembly comprising a base, a first cover, a second cover, a third cover, a first electrode, and a core module, the first, second, third covers cover the base to form a receiving chamber to accommodate the core module, the first electrode extended through the base and electronically connected to the core module;

a wearable assembly, the wearable assembly detachably connected to the signal capturing assembly through the at least one port; and wherein the first cover serves as a second electrode electronically connected to the core module, the first cover defines a button configured for labeling a contact position of the first cover, when the button is pressed, a loop is formed between the first electrode and the second electrode so that the first electrode detects vital signs of an user and transmits the detected vital signs to the core module.

2. The wearable electronic device of claim 1, wherein the first cover defines a first port at an end of the first cover, the third cover defines a second port at an end of the third cover, the second port is electronically connected to the core module.

3. The wearable electronic device of claim 1, wherein the wearable assembly is a wrist assembly, the wrist assembly comprises a first band and a second band, the first band comprises a first connector detachably latched to the first port and a plurality of positioning holes, the second band comprises a second connector detachably latched to the second port and a plurality of positioning members engaging with the plurality of positioning holes.

4. The wearable electronic device of claim 1, wherein the wearable assembly is a holder, the holder comprises a case and a latching member, the case defines a receiving slot configured for receiving the signal capturing assembly and a through hole at an end of the case, the latching member is secured on a bottom surface of the case with a latching portion exposed from the through hole for latching to the first port.

5. The wearable electronic device of claim 4, wherein the holder further comprises a convertor arranged at another end of the case opposite to the through hole and configured to connect to the second port of the signal capturing assembly; the convertor comprises two contacting rods protruding from the case configured for electrically connecting to core module.

6. The wearable electronic device of claim 5, wherein the holder further comprises two connecting electrodes arranged on the bottom surface of the case, the connecting electrodes are electronically connected to the contacting rods and configured for integrating the signal capturing assembly to clothes of the user.

7. The wearable electronic device of claim 1, further comprising an accessory, wherein the accessory comprises a first connecting portion, a cable, and a second connecting portion; the first and second connecting portions are connected to two opposite ends of the cable, the first connecting portion is detachably connected to the signal capturing assembly, the second connecting portion is configured for connecting the signal capturing assembly to charge or to other electronic device.

8. A wearable electronic device comprising:
a signal capturing assembly configured for detecting and processing vital signs from a user; a wrist assembly configured for attaching the signal capturing assembly to wrists of the user; and a holder configured for attaching the signal capturing assembly to clothes of the user; wherein the signal capturing assembly is detachably connected to one of the wrist assembly and the holder; wherein the signal capturing assembly comprises a base, a first cover, a second cover, a third cover, a first electrode, and a core module, the first, second, third covers cover the base to form a receiving chamber to accommodate the core module, the first electrode is extended through the base and electronically connected to the core module; wherein the first cover defines a first port at an end of the first cover, the third cover defines a second port at an end of the third cover, the second port is electronically connected to the core module.

9. The wearable electronic device of claim 8, wherein the first cover serves as a second electrode electronically connected to the core module, the first cover defines a button configured for labeling a contact position of the first cover, when the button is pressed, a loop is formed between the first electrode and the second electrode so that the first electrode detects vital signs of an user and transmits the detected vital signs to the core module.

10. The wearable electronic device of claim 8, further comprising an accessory, wherein the accessory comprises a first connecting portion, a cable, and a second connecting portion; the first and second connecting portions are connected to two opposite ends of the cable, the first connecting portion is detachably connected to the signal capturing assembly, the second connecting portion is configured for connecting the signal capturing assembly to charge or connecting the signal capturing assembly to other electronic device.

11. The wearable electronic device of claim 8, wherein the wrist assembly comprises a first band and a second band, the first band comprises a first connector detachably latched to the first port and a plurality of positioning holes, the second band comprises a second connector detachably latched to the second port and a plurality of positioning members engaging with the plurality of positioning holes.

12. The wearable electronic device of claim 11, wherein the holder further comprises a convertor arranged at another end of the case opposite to the through hole and configured to connect to the second port of the signal capturing assembly; the convertor comprises two contacting rods protruding from the case configured for electrically connecting to core module.

13. The wearable electronic device of claim 12, wherein the holder further comprises two connecting electrodes arranged on the bottom surface of the case, the connecting electrodes are electronically connected to the contacting rods and configured for integrating the signal capturing assembly to the clothes of the user.

14. The wearable electronic device of claim 8, wherein the wrist assembly is a holder, the holder comprises a case and a latching member, the case defines a receiving slot configured for receiving the signal capturing assembly and a through hole at an end of the case, the latching member is secured on a bottom surface of the case with a latching portion exposed from the through hole for latching to the first port.

15. A wearable electronic device, comprising:
a vital signals monitor configured to detect human vital signs through physical contact and having first and second connection points, the monitor including a data port mounted adjacent the first connection point;
a detachable limb connector, including at least one strap, configured to attach the monitor to a limb, the detachable limb connector being configured to connect to the monitor at the first and second connection points;
wherein when the detachable limb connector is disconnected from the first connection point the data port is physically accessible such that data from the monitor can be downloaded through the data port;

wherein when the detachable limb connector is connected to the first connection point, the data port is physically blocked and inaccessible for data download.

\* \* \* \* \*